(12) United States Patent
Braun et al.

(10) Patent No.: US 7,934,284 B2
(45) Date of Patent: May 3, 2011

(54) TOOTHBRUSHES

(75) Inventors: Phillip M. Braun, Exeter, RI (US); William R. Brown, Jr., Peabody, MA (US); Alexander T. Chenvainu, Sudbury, MA (US); Thomas A. Christman, Lexington, MA (US)

(73) Assignee: Braun GmbH, Kronberg (DE)

( * ) Notice: Subject to any disclaimer, the term of this patent is extended or adjusted under 35 U.S.C. 154(b) by 893 days.

(21) Appl. No.: 10/364,148

(22) Filed: Feb. 11, 2003

(65) Prior Publication Data

US 2004/0154112 A1 Aug. 12, 2004

(51) Int. Cl.
*A46B 9/06* (2006.01)

(52) U.S. Cl. ............... 15/22.1; 15/110; 15/167.1; 15/28

(58) Field of Classification Search ............ 15/22.1, 15/28, 110, 167.1, 170; 433/127, 166; 601/139, 601/141

See application file for complete search history.

(56) References Cited

U.S. PATENT DOCUMENTS

| | | | |
|---|---|---|---|
| 34,109 A | 1/1862 | Fanshaw et al. |
| 90,763 A | 6/1869 | Marshall |
| 116,030 A | 6/1871 | Devines |
| 218,431 A | 8/1879 | Dunham |
| 301,644 A | 7/1884 | Thompson |
| 411,910 A | 10/1889 | Van Horne |
| 742,639 A | 10/1903 | Harlan |
| 907,842 A | 12/1908 | Meuzies |
| 915,251 A | 3/1909 | Vanderslice |
| 1,006,630 A | 10/1911 | Clarke |
| 1,022,920 A | 4/1912 | Anderson |
| 1,128,139 A | 2/1915 | Hoffman |
| 1,191,556 A | 7/1916 | Blake |
| 1,251,250 A | 12/1917 | Libby |
| 1,268,544 A | 6/1918 | Cates |
| 1,297,272 A | 3/1919 | Pollock |
| 1,327,757 A | 1/1920 | Eggers |
| 1,405,279 A | 1/1922 | Cassedy |
| 1,526,267 A | 2/1925 | Dessau |
| 1,578,074 A | 3/1926 | Chandler |
| 1,588,785 A | 6/1926 | Van Sant |
| 1,598,224 A | 8/1926 | Van Sant |
| 1,673,638 A | 6/1928 | Peterson |
| 1,691,863 A | 11/1928 | Van Sant |
| 1,704,564 A | 3/1929 | Friedland |

(Continued)

FOREIGN PATENT DOCUMENTS

| | | |
|---|---|---|
| CN | 1182354 C | 5/1998 |
| CN | 1248151 C | 3/2000 |
| CN | 1328425 | 12/2001 |
| CN | 1359272 | 7/2002 |
| DE | 1992022 | 8/1968 |
| DE | 2526893 | 12/1976 |
| DE | 2 402 785 | 3/1979 |
| DE | 4201873 | 5/1993 |
| DE | 4303431 | 8/1993 |

(Continued)

OTHER PUBLICATIONS

Web page document www.sullivanschein.com "Densco Prophy Cups Waterpik Technologies" Preventives p. 421.

(Continued)

*Primary Examiner* — Laura C Guidotti
(74) *Attorney, Agent, or Firm* — Calfee, Halter & Griswold LLP

(57) ABSTRACT

Toothbrush heads, e.g., for power toothbrushes, are provided. The toothbrush heads include a support member, a resilient member extending from the support member, and a plurality of tufts of bristles extending from the support member and at least partially surrounding the member. The resilient member may be cup-shaped, fan-shaped, or textured.

16 Claims, 11 Drawing Sheets

U.S. PATENT DOCUMENTS

| | | | |
|---|---|---|---|
| 1,705,249 A | 3/1929 | Henry | |
| 1,720,017 A | 7/1929 | Touchstone | |
| 1,764,130 A | 6/1930 | Vardeman | |
| 1,796,893 A | 3/1931 | McVeigh | |
| 1,797,946 A | 3/1931 | Eichel | |
| 1,833,555 A | 11/1931 | Bell | |
| 1,852,480 A | 5/1932 | Ruetz | |
| 1,961,347 A | 5/1932 | Johnson | |
| 1,868,893 A | 7/1932 | Gentle | |
| 1,890,894 A | 12/1932 | Arnold et al. | |
| 1,901,230 A | 3/1933 | Duey | |
| 1,907,286 A | 5/1933 | Chott | |
| 1,919,414 A | 5/1933 | Varga | |
| 1,924,152 A | 8/1933 | Coney et al. | |
| 1,935,099 A * | 11/1933 | O'Donnell | 15/188 |
| 1,935,417 A | 11/1933 | Gavney et al. | |
| 1,950,318 A | 3/1934 | McNab | |
| 1,963,389 A | 6/1934 | Vardeman | |
| 1,965,009 A | 7/1934 | Stevens | |
| 1,993,662 A | 3/1935 | Green | |
| 2,039,278 A | 5/1936 | Blanchard | |
| 2,042,239 A | 5/1936 | Planding | |
| 2,155,473 A | 9/1936 | Coleman | |
| 2,059,914 A | 11/1936 | Rosenberg | |
| 2,088,839 A | 8/1937 | Coney et al. | |
| 2,093,007 A | 9/1937 | Chott | |
| 2,117,174 A | 5/1938 | Jones | |
| 2,129,082 A | 9/1938 | Bryer | |
| 2,139,245 A | 12/1938 | Ogden | |
| 2,146,455 A | 2/1939 | Tepper | |
| 2,149,950 A | 3/1939 | Axline | |
| 2,154,846 A | 4/1939 | Heymann et al. | |
| 2,176,309 A | 10/1939 | Love et al. | |
| 2,189,175 A | 2/1940 | Jackson | |
| 2,206,726 A | 7/1940 | Lasater | |
| 2,219,753 A | 10/1940 | Seguin | |
| 2,220,053 A | 10/1940 | Pruner | |
| 2,225,331 A | 12/1940 | Campbell | |
| 2,226,145 A | 12/1940 | Smith | |
| 2,226,663 A | 12/1940 | Hill et al. | |
| 2,244,699 A | 6/1941 | Hosey | |
| 2,246,867 A | 6/1941 | Thomas et al. | 15/110 |
| 2,279,355 A | 4/1942 | Wilensky | |
| 2,294,900 A | 9/1942 | Fuller | |
| 2,312,828 A | 3/1943 | Adamsson | |
| 2,326,632 A | 8/1943 | Friedman | |
| 2,328,998 A | 9/1943 | Radford | |
| 2,334,796 A | 11/1943 | Steinmetz et al. | |
| 2,364,205 A | 12/1944 | Fuller | |
| 2,443,461 A | 6/1948 | Kempster | |
| 2,512,059 A | 6/1950 | Haeusser | |
| 2,516,491 A | 7/1950 | Swasick | |
| 2,534,086 A | 12/1950 | Vosbikian et al. | |
| 2,545,814 A | 3/1951 | Kempster | |
| 2,637,870 A | 5/1953 | Cohen | |
| 2,684,063 A | 7/1954 | Bileth | |
| 2,702,914 A | 3/1955 | Kittle et al. | 15/114 |
| 2,757,668 A | 8/1956 | Meyer-Saladin | |
| 2,789,352 A | 4/1957 | Wiseman | |
| 2,815,601 A | 12/1957 | Hough, Jr. | |
| 2,819,482 A | 1/1958 | Applegate | |
| 2,941,225 A | 6/1960 | Paul | |
| 2,987,742 A | 6/1961 | Kittle et al. | |
| 3,007,441 A | 11/1961 | Eyer | |
| 3,016,554 A | 1/1962 | Peterson | |
| 3,050,072 A | 8/1962 | Diener | |
| 3,103,027 A | 9/1963 | Birch | |
| 3,110,052 A | 11/1963 | Whitman | |
| 3,128,487 A | 4/1964 | Vallis | |
| 3,129,499 A | 4/1964 | Cyzer | |
| 3,133,546 A | 5/1964 | Dent | |
| 3,181,193 A | 5/1965 | Nobles et al. | |
| 3,195,537 A | 7/1965 | Blasi | 128/56 |
| 3,196,299 A * | 7/1965 | Kott | 310/81 |
| 3,199,139 A | 8/1965 | Vallis | |
| 3,230,562 A | 1/1966 | Birch | 15/110 |
| D204,581 S | 4/1966 | Coulson | |
| 3,258,805 A | 7/1966 | Rossman | |
| 3,261,354 A | 7/1966 | Shpuntoff | |
| 3,295,156 A | 1/1967 | Brant | |
| 3,302,230 A | 2/1967 | Poppelman | |
| 3,316,576 A | 5/1967 | Urbush | |
| 3,327,339 A | 6/1967 | Lemelson | |
| 3,359,588 A | 12/1967 | Kobler | 15/110 |
| 3,403,070 A | 9/1968 | Lewis, Jr. | |
| 3,411,979 A | 11/1968 | Lewis, Jr. | |
| 3,491,396 A | 1/1970 | Hesene | |
| 3,553,759 A | 1/1971 | Kramer et al. | |
| 3,613,143 A | 10/1971 | Muhler et al. | |
| 3,633,237 A | 1/1972 | Bagube | 15/188 |
| 3,647,610 A | 3/1972 | Wolf | |
| 3,677,264 A | 7/1972 | Brockman | |
| 3,939,522 A | 2/1976 | Shimizu | |
| 3,959,842 A | 6/1976 | Alley | |
| 3,969,783 A | 7/1976 | Shipman | |
| 3,977,084 A | 8/1976 | Sloan | 32/59 |
| 3,992,747 A | 11/1976 | Hufton | |
| 4,033,008 A | 7/1977 | Warren et al. | |
| 4,081,877 A | 4/1978 | Vitale | 15/188 |
| 4,115,893 A | 9/1978 | Nakata et al. | |
| 4,128,910 A | 12/1978 | Nakata et al. | 15/110 |
| 4,263,691 A | 4/1981 | Pakarnseree | |
| 4,277,862 A | 7/1981 | Weideman | |
| 4,288,883 A | 9/1981 | Dolinsky | |
| 4,356,585 A | 11/1982 | Protell et al. | |
| 4,391,951 A | 7/1983 | Scheetz | |
| 4,399,582 A | 8/1983 | Ernest et al. | 15/176 |
| 4,403,623 A | 9/1983 | Mark | |
| 4,428,091 A | 1/1984 | Janssen | 15/167 A |
| 4,432,114 A | 2/1984 | Goudsmit | 15/104.93 |
| 4,432,729 A | 2/1984 | Fattaleh | 433/118 |
| 4,472,853 A | 9/1984 | Rauch | |
| 4,476,280 A | 10/1984 | Poppe et al. | |
| 4,480,351 A | 11/1984 | Koffler | |
| 4,525,531 A | 6/1985 | Zukosky et al. | |
| 4,538,631 A | 9/1985 | Prince | |
| 4,571,768 A | 2/1986 | Kawashima | |
| 4,573,920 A | 3/1986 | d'Argembeau | |
| 4,585,416 A | 4/1986 | DeNiro et al. | |
| 4,603,166 A | 7/1986 | Poppe et al. | |
| 4,616,064 A | 10/1986 | Zukosky et al. | |
| 4,617,342 A | 10/1986 | Poppe et al. | |
| 4,617,694 A | 10/1986 | Bori | |
| 4,623,495 A | 11/1986 | Degoix et al. | |
| 4,628,564 A | 12/1986 | Youssef | |
| 4,672,706 A | 6/1987 | Hill | |
| 4,691,405 A | 9/1987 | Reed | |
| 4,720,489 A | 1/1988 | Shander | |
| 4,763,380 A | 8/1988 | Sandvick | |
| 4,802,255 A | 2/1989 | Breuer et al. | |
| 4,812,070 A | 3/1989 | Marty | |
| 4,827,551 A | 5/1989 | Maser et al. | |
| 4,854,870 A | 8/1989 | Kofod | |
| 4,866,806 A | 9/1989 | Bedford | |
| 4,929,180 A * | 5/1990 | Moreschini | 433/166 |
| 4,974,615 A | 12/1990 | Doundoulakis | |
| 5,005,246 A | 4/1991 | Yen-Hui | |
| 5,027,463 A | 7/1991 | Daub | |
| 5,032,082 A | 7/1991 | Herrera | |
| 5,040,260 A | 8/1991 | Michaels | |
| 5,058,230 A | 10/1991 | Hodosh et al. | |
| 5,137,039 A | 8/1992 | Klinkhammer | |
| 5,144,712 A | 9/1992 | Hansel et al. | |
| 5,211,494 A | 5/1993 | Baijnath | |
| 5,226,197 A | 7/1993 | Nack et al. | |
| 5,249,327 A | 10/1993 | Spisich | |
| 5,315,731 A | 5/1994 | Millar | 15/167.1 |
| 5,323,795 A | 6/1994 | Berens | |
| 5,335,389 A | 8/1994 | Curtis et al. | |
| 5,345,644 A | 9/1994 | Spisich | |
| 5,347,676 A | 9/1994 | Saitoh | |
| 5,348,473 A | 9/1994 | Kivlighan, Jr. | 433/114 |
| 5,360,339 A * | 11/1994 | Rosenberg | 433/165 |
| 5,378,153 A * | 1/1995 | Giuliani et al. | 433/216 |
| 5,392,482 A | 2/1995 | Drulias et al. | |
| 5,392,483 A | 2/1995 | Heinzelman et al. | 15/167.1 |
| 5,440,774 A | 8/1995 | Cole | |

| | | | |
|---|---|---|---|
| 5,446,940 A | 9/1995 | Curtis et al. | |
| 5,467,495 A | 11/1995 | Boland et al. | |
| 5,491,863 A | 2/1996 | Dunn | |
| 5,497,526 A | 3/1996 | Klinkhammer | |
| 5,528,793 A | 6/1996 | Schbot | |
| 5,535,474 A | 7/1996 | Salazar | |
| 5,564,150 A | 10/1996 | Ciccotelli | |
| 5,584,690 A * | 12/1996 | Maassarani | 433/125 |
| D378,166 S | 2/1997 | Savitt et al. | |
| 5,604,951 A | 2/1997 | Shipp | |
| 5,628,082 A | 5/1997 | Moskovich | |
| 5,648,394 A | 7/1997 | Boxall et al. | |
| 5,652,990 A | 8/1997 | Driesen et al. | 15/28 |
| 5,669,097 A | 9/1997 | Klinkhammer | |
| 5,689,850 A | 11/1997 | Shekalim | |
| 5,700,146 A | 12/1997 | Kucar | |
| 5,711,759 A | 1/1998 | Smith et al. | |
| 5,735,011 A | 4/1998 | Asher | |
| 5,758,383 A | 6/1998 | Hohlbein | |
| 5,799,353 A | 9/1998 | Oishi et al. | |
| 5,802,656 A | 9/1998 | Dawson et al. | |
| 5,806,127 A | 9/1998 | Samoil et al. | |
| 5,813,079 A | 9/1998 | Halm | |
| 5,836,033 A | 11/1998 | Berge | |
| 5,851,551 A | 12/1998 | Tseng et al. | |
| 5,860,183 A | 1/1999 | Kam | |
| 5,864,915 A | 2/1999 | Ra | |
| 5,878,459 A | 3/1999 | McParland | |
| 5,881,425 A | 3/1999 | Hudson et al. | 15/167.1 |
| 5,896,614 A | 4/1999 | Flewitt | |
| 5,903,949 A | 5/1999 | Halm | |
| 5,921,255 A | 7/1999 | Garita | |
| 5,926,900 A | 7/1999 | Bennett | |
| D413,384 S | 8/1999 | Hanley et al. | |
| D413,385 S | 8/1999 | Hanley et al. | |
| 5,930,860 A | 8/1999 | Shipp | |
| 5,946,758 A | 9/1999 | Hohlbein et al. | |
| 5,946,759 A | 9/1999 | Cann | |
| 5,966,771 A | 10/1999 | Stoud | |
| 5,970,564 A | 10/1999 | Inns et al. | 15/201 |
| 5,980,542 A | 11/1999 | Saldivar | |
| 5,987,688 A | 11/1999 | Roberts et al. | 15/167.1 |
| 5,991,958 A | 11/1999 | Hohlbein | |
| 5,991,959 A | 11/1999 | Raven et al. | |
| 6,003,189 A | 12/1999 | Falleiros | |
| 6,021,538 A | 2/2000 | Kressner et al. | 15/28 |
| 6,021,541 A | 2/2000 | Mori et al. | |
| 6,032,322 A | 3/2000 | Forsline | |
| 6,041,467 A | 3/2000 | Roberts et al. | |
| 6,041,468 A | 3/2000 | Chen et al. | |
| 6,044,514 A | 4/2000 | Kaneda | |
| 6,058,541 A | 5/2000 | Masterman et al. | 15/28 |
| 6,065,890 A | 5/2000 | Weitz | |
| 6,067,684 A | 5/2000 | Kweon | 15/167.1 |
| 6,073,299 A | 6/2000 | Hohlbein | |
| 6,077,360 A | 6/2000 | Takashima | |
| 6,092,252 A | 7/2000 | Fischer et al. | |
| 6,098,233 A | 8/2000 | Chen | |
| 6,099,309 A | 8/2000 | Cardarelli | 433/125 |
| 6,101,659 A | 8/2000 | Halm | |
| 6,108,849 A | 8/2000 | Weihrauch | |
| 6,108,854 A | 8/2000 | Dingert | |
| 6,115,870 A | 9/2000 | Solanki et al. | |
| 6,126,533 A | 10/2000 | Johnson et al. | |
| 6,138,316 A | 10/2000 | Weihrauch | |
| D434,231 S | 11/2000 | Chen | |
| 6,146,140 A * | 11/2000 | Bailey | 433/166 |
| 6,151,745 A | 11/2000 | Roberts et al. | |
| 6,151,746 A | 11/2000 | Lewis | |
| 6,168,434 B1 | 1/2001 | Diggelen | |
| 6,176,631 B1 | 1/2001 | Gueret | |
| 6,178,582 B1 | 1/2001 | Halm | |
| 6,182,323 B1 | 2/2001 | Bahten | |
| 6,182,365 B1 | 2/2001 | Tseng et al. | |
| 6,185,779 B1 | 2/2001 | Kramer | |
| 6,190,367 B1 | 2/2001 | Hall | |
| 6,192,544 B1 | 2/2001 | Persidsky et al. | |
| 6,219,874 B1 | 4/2001 | Van Gelder et al. | |
| 6,234,798 B1 | 5/2001 | Beals et al. | |
| 6,237,178 B1 | 5/2001 | Krammer et al. | 15/22.1 |
| D443,418 S | 6/2001 | Chen | |
| 6,240,590 B1 | 6/2001 | Nesbit | |
| 6,245,032 B1 | 6/2001 | Sauer et al. | |
| 6,253,404 B1 | 7/2001 | Boland et al. | |
| 6,253,405 B1 | 7/2001 | Gutelius et al. | |
| 6,254,390 B1 | 7/2001 | Wagner | |
| 6,272,713 B1 | 8/2001 | Lotwin | |
| 6,273,719 B1 | 8/2001 | Whitman | |
| 6,276,019 B1 | 8/2001 | Leversby et al. | |
| 6,276,020 B1 | 8/2001 | Leversby et al. | |
| 6,276,021 B1 | 8/2001 | Hohlbein | |
| 6,308,367 B1 | 10/2001 | Beals et al. | |
| 6,311,358 B1 | 11/2001 | Soetewey et al. | |
| 6,311,360 B1 | 11/2001 | Lanvers | |
| 6,314,605 B1 | 11/2001 | Solanki et al. | |
| 6,314,606 B1 | 11/2001 | Hohlbein | |
| 6,319,332 B1 | 11/2001 | Gavney et al. | |
| 6,325,626 B1 | 12/2001 | Blass | |
| 6,334,231 B2 | 1/2002 | Safieh | |
| 6,347,425 B1 | 2/2002 | Fattori et al. | |
| 6,353,958 B2 | 3/2002 | Weihrauch | |
| 6,357,074 B1 | 3/2002 | Weihrauch | |
| 6,371,294 B1 | 4/2002 | Blaustein et al. | |
| 6,374,448 B2 | 4/2002 | Seifert | |
| 6,374,449 B1 | 4/2002 | Jolly | |
| 6,389,634 B1 | 5/2002 | Devlin et al. | 15/110 |
| 6,408,473 B1 | 6/2002 | Kessler | |
| 6,408,476 B1 | 6/2002 | Cann | |
| D459,892 S | 7/2002 | Eliav et al. | |
| 6,442,786 B1 | 9/2002 | Halm et al. | |
| 6,442,787 B2 | 9/2002 | Hohlbein | |
| 6,446,295 B1 | 9/2002 | Calabrese | |
| 6,463,618 B1 | 10/2002 | Zimmer | 15/110 |
| 6,463,619 B2 | 10/2002 | Gavney | |
| 6,490,747 B1 | 12/2002 | Metwally | |
| 6,502,272 B1 | 1/2003 | Fox et al. | |
| 6,505,373 B2 | 1/2003 | Van Gelder et al. | |
| 6,510,575 B2 | 1/2003 | Kataoka | |
| 6,513,182 B1 * | 2/2003 | Calabrese et al. | 15/110 |
| 6,514,445 B1 | 2/2003 | Cann et al. | |
| 6,536,068 B1 | 3/2003 | Weihrauch | |
| 6,546,583 B1 | 4/2003 | Rhrig | |
| 6,546,586 B2 | 4/2003 | Cho | |
| 6,547,750 B2 | 4/2003 | Huang | |
| 6,553,604 B1 | 4/2003 | Braun et al. | |
| 6,554,614 B1 | 4/2003 | Dubbe et al. | |
| 6,568,020 B1 | 5/2003 | Hosokawa | |
| D476,157 S | 6/2003 | Gatzemeyer et al. | |
| 6,571,417 B1 * | 6/2003 | Gavney et al. | 15/117 |
| 6,599,048 B2 | 7/2003 | Kuo | |
| 6,612,770 B2 | 9/2003 | Aoyama | |
| 6,618,893 B2 | 9/2003 | Wang | |
| 6,654,979 B2 | 12/2003 | Calabrese | |
| 6,658,688 B2 | 12/2003 | Gavney, Jr. | 15/117 |
| 6,665,901 B2 | 12/2003 | Driesen et al. | |
| 6,668,416 B2 | 12/2003 | Georgi et al. | |
| 6,671,919 B2 | 1/2004 | Davis | |
| 6,675,428 B2 | 1/2004 | Halm | |
| 6,687,940 B1 | 2/2004 | Gross et al. | |
| 6,694,559 B1 | 2/2004 | Sloan | |
| 6,708,364 B2 | 3/2004 | Huber | |
| 6,721,987 B2 | 4/2004 | McDevitt et al. | |
| 6,725,493 B2 | 4/2004 | Calabrese et al. | |
| RE38,521 E | 5/2004 | Halm | |
| 6,735,808 B2 | 5/2004 | Chen | |
| 6,743,822 B2 | 6/2004 | Styczynski et al. | |
| 6,766,548 B1 | 7/2004 | Lukas et al. | |
| 6,772,465 B2 | 8/2004 | Mehta | |
| 6,779,851 B2 | 8/2004 | Bouchiere | |
| 6,792,642 B2 | 9/2004 | Wagstaff | |
| 6,793,434 B1 | 9/2004 | Olson | |
| 6,802,097 B2 | 10/2004 | Hfliger et al. | |
| 6,805,557 B2 | 10/2004 | Davies et al. | |
| 6,807,703 B2 | 10/2004 | Van Gelder et al. | |
| 6,808,068 B2 | 10/2004 | Abada | |
| 6,810,551 B1 | 11/2004 | Weihrauch | |
| 6,813,793 B2 | 11/2004 | Eliav | |
| 6,813,794 B2 | 11/2004 | Weng | |

| | | | | | |
|---|---|---|---|---|---|
| 6,817,054 B2 | 11/2004 | Moskovich et al. | 2001/0003600 A1 | 6/2001 | Guay .................... 427/2.29 |
| 6,820,299 B2 | 11/2004 | Gavney, Jr. ............... 15/117 | 2001/0008032 A1 | 7/2001 | Llewellyn-Jones et al. |
| 6,820,300 B2 | 11/2004 | Gavney, Jr. ............... 15/117 | 2001/0023516 A1 | 9/2001 | Driesen et al. |
| 6,823,554 B1 | 11/2004 | Braun et al. | 2001/0039689 A1 | 11/2001 | Gavney |
| 6,826,797 B1 | 12/2004 | Chenvainu et al. | 2002/0056197 A1 | 5/2002 | Johnson |
| 6,832,819 B1 | 12/2004 | Weihrauch | 2002/0059685 A1 | 5/2002 | Paffrath |
| D501,601 S | 2/2005 | Brown, Jr. et al. | 2002/0084550 A1 | 7/2002 | Roberts et al. |
| D501,605 S | 2/2005 | Brown, Jr. et al. | 2002/0100134 A1 | 8/2002 | Dunn et al. |
| 6,851,150 B2 | 2/2005 | Chiang | 2002/0116775 A1 | 8/2002 | Wong ..................... 15/22.1 |
| 6,851,431 B2 | 2/2005 | Mayeri | 2002/0138926 A1 | 10/2002 | Brown, Jr. et al. ......... 15/22.1 |
| 6,859,968 B2 | 3/2005 | Miller et al. | 2002/0138931 A1 | 10/2002 | Davies |
| 6,859,969 B2 | 3/2005 | Gavney, Jr. et al. ......... 15/117 | 2002/0152564 A1 | 10/2002 | Blaustein et al. |
| 6,862,771 B1 | 3/2005 | Muller | 2002/0157202 A1 | 10/2002 | Hartel |
| 6,865,767 B1 | 3/2005 | Gavney | 2003/0009837 A1 | 1/2003 | Cann |
| 6,871,374 B2 | 3/2005 | Brezler et al. | 2003/0014826 A1 | 1/2003 | Touzani |
| 6,874,194 B1 | 4/2005 | Harris | 2003/0019060 A1 | 1/2003 | Gavney |
| 6,883,200 B1 | 4/2005 | Euler | 2003/0033680 A1* | 2/2003 | Davies et al. ............. 15/22.1 |
| 6,886,207 B1 | 5/2005 | Solanki | 2003/0033682 A1 | 2/2003 | Davies et al. ............. 15/110 |
| 6,886,208 B2 | 5/2005 | Kemp et al. | 2003/0036561 A1 | 2/2003 | Styczynski et al. |
| 6,889,401 B2 | 5/2005 | Fattori et al. | 2003/0041021 A1 | 3/2003 | Stein et al. |
| 6,892,412 B2 | 5/2005 | Gatzemeyer et al. | 2003/0077107 A1 | 4/2003 | Kuo ...................... 401/278 |
| 6,895,624 B2 | 5/2005 | Fischer et al. | 2003/0140437 A1 | 7/2003 | Eliav |
| 6,907,638 B2 | 6/2005 | Katz | 2003/0140440 A1 | 7/2003 | Gavney, Jr. ............... 15/117 |
| 6,920,659 B2 | 7/2005 | Cacka et al. | 2003/0140442 A1 | 7/2003 | Aoyama |
| 6,931,688 B2 | 8/2005 | Moskovich et al. | 2003/0154567 A1 | 8/2003 | Drossler et al. |
| 6,932,216 B2 | 8/2005 | Blaustein et al. | 2003/0159224 A1 | 8/2003 | Fischer et al. ............. 15/110 |
| 6,938,293 B2 | 9/2005 | Eliav et al. | 2003/0163882 A1 | 9/2003 | Blaustein et al. |
| 6,938,294 B2 | 9/2005 | Fattori et al. | 2003/0182743 A1 | 10/2003 | Gatzemeyer et al. ......... 15/22.1 |
| 6,944,901 B2 | 9/2005 | Gatzemeyer et al. | 2003/0182746 A1 | 10/2003 | Shortt et al. |
| 6,944,903 B2 | 9/2005 | Gavney | 2003/0196283 A1 | 10/2003 | Eliav et al. .............. 15/22.1 |
| 6,948,209 B2 | 9/2005 | Chan | 2003/0208870 A1 | 11/2003 | Jimenez |
| 6,954,961 B2 | 10/2005 | Ferber et al. | 2003/0213075 A1 | 11/2003 | Hui et al. |
| 6,957,467 B2 | 10/2005 | Cabedo-Deslierres et al. | 2003/0226223 A1 | 12/2003 | Chan |
| 6,957,469 B2 | 10/2005 | Davies | 2003/0229959 A1* | 12/2003 | Gavney et al. ............. 15/117 |
| 6,958,562 B1 | 11/2005 | Kaizuka | 2004/0006837 A1 | 1/2004 | Cann |
| 6,964,603 B2 | 11/2005 | Fischer et al. | 2004/0010869 A1 | 1/2004 | Fattori et al. ............. 15/22.1 |
| 6,966,093 B2 | 11/2005 | Eliav et al. | 2004/0010870 A1 | 1/2004 | McNair |
| 6,968,590 B2 | 11/2005 | Ponzini | 2004/0025272 A1 | 2/2004 | Stvartak et al. |
| 6,983,507 B2 | 1/2006 | McDougall | 2004/0025274 A1 | 2/2004 | Moskovich et al. |
| 6,988,292 B1 | 1/2006 | Wang | 2004/0025275 A1 | 2/2004 | Moskovich et al. ......... 15/167.1 |
| 6,990,706 B2 | 1/2006 | Broecker et al. | 2004/0031115 A1 | 2/2004 | Gavney, Jr. ............... 15/117 |
| 6,993,804 B1 | 2/2006 | Braun et al. | 2004/0045105 A1 | 3/2004 | Eliav et al. .............. 15/22.1 |
| 6,996,870 B2 | 2/2006 | Hohlbein | 2004/0060132 A1 | 4/2004 | Gatzemeyer et al. ......... 15/22.1 |
| 7,003,839 B2 | 2/2006 | Hafliger et al. | 2004/0060133 A1 | 4/2004 | Eliav .................... 15/22.1 |
| 7,007,332 B2 | 3/2006 | Hohlbein | 2004/0060135 A1 | 4/2004 | Gatzemeyer et al. |
| 7,007,335 B1 | 3/2006 | Doat | 2004/0060136 A1 | 4/2004 | Gatzemeyer et al. |
| 7,013,522 B2 | 3/2006 | Kumagai | 2004/0060137 A1 | 4/2004 | Eliav .................... 15/22.1 |
| 7,020,925 B1 | 4/2006 | Gitelis | 2004/0068811 A1 | 4/2004 | Fulop et al. |
| 7,020,928 B2 | 4/2006 | Hohlbein ............... 15/167.1 | 2004/0074034 A1 | 4/2004 | Russell |
| 7,024,720 B2 | 4/2006 | Moskovich et al. | 2004/0074035 A1 | 4/2004 | Huang |
| 7,036,179 B1 | 5/2006 | Weihrauch | 2004/0087882 A1 | 5/2004 | Roberts et al. |
| 7,039,984 B1 | 5/2006 | Watanabe et al. | 2004/0088807 A1 | 5/2004 | Blaustein et al. |
| 7,047,589 B2 | 5/2006 | Gavney, Jr. ............... 15/110 | 2004/0088812 A1 | 5/2004 | Weihrauch |
| 7,047,591 B2 | 5/2006 | Hohlbein | 2004/0134007 A1 | 7/2004 | Wong |
| 7,051,394 B2 | 5/2006 | Gavney, Jr. | 2004/0154112 A1 | 8/2004 | Braun et al. ............. 15/22.1 |
| 7,055,205 B2 | 6/2006 | Aoyama | 2004/0154118 A1 | 8/2004 | Bohn |
| 7,069,615 B2 | 7/2006 | Gavney | 2004/0168271 A1 | 9/2004 | McDougall ................ 15/28 |
| 7,073,255 B1 | 7/2006 | Ford | 2004/0177462 A1 | 9/2004 | Brown et al. |
| 7,086,116 B2 | 8/2006 | Broecker et al. | 2004/0187887 A1 | 9/2004 | Beckmann |
| 7,089,621 B2 | 8/2006 | Hohlbein | 2004/0200016 A1 | 10/2004 | Blaustein et al. |
| 7,111,350 B2 | 9/2006 | Blackman et al. | 2004/0200748 A1 | 10/2004 | Klassen et al. |
| 7,117,555 B2 | 10/2006 | Fattori et al. | 2004/0211018 A1 | 10/2004 | Canton |
| 6,988,777 B2 | 11/2006 | Pfenniger et al. | 2004/0221409 A1 | 11/2004 | Gavney, Jr. ............... 15/117 |
| 7,137,163 B2 | 11/2006 | Gatzemeyer et al. | 2004/0231076 A1 | 11/2004 | Gavney, Jr. ............... 15/22.1 |
| 7,140,058 B2 | 11/2006 | Gatzemeyer et al. | 2004/0231082 A1 | 11/2004 | Gavney, Jr. ............... 15/110 |
| 7,143,462 B2 | 12/2006 | Hohlbein | 2004/0237226 A1 | 12/2004 | Hohlbein et al. |
| 7,160,508 B2 | 1/2007 | Lee | 2004/0237236 A1 | 12/2004 | Gavney, Jr. ............... 15/117 |
| 7,162,767 B2 | 1/2007 | Pfenniger et al. | 2004/0255416 A1 | 12/2004 | Hohlbein |
| 7,174,596 B2 | 2/2007 | Fischer et al. | 2004/0255427 A1 | 12/2004 | Gavney |
| 7,181,799 B2 | 2/2007 | Gavney et al. | 2004/0261207 A1 | 12/2004 | Gavney |
| 7,185,383 B2 | 3/2007 | Gatzemeyer et al. | 2005/0000043 A1 | 1/2005 | Chan et al. |
| 7,210,184 B2 | 5/2007 | Eliav et al. | 2005/0011024 A1 | 1/2005 | Ping et al. |
| 7,226,555 B2 | 6/2007 | Weihrauch | 2005/0015901 A1 | 1/2005 | Gavney, Jr. ................ 15/28 |
| 7,228,583 B2 | 6/2007 | Chan et al. | 2005/0015904 A1 | 1/2005 | Gavney |
| 7,322,067 B2 | 1/2008 | Hohlbein | 2005/0015907 A1 | 1/2005 | Georgi et al. |
| 7,392,562 B2 | 7/2008 | Boland et al. | 2005/0022322 A1 | 2/2005 | Jimenez et al. |
| 7,546,658 B2 | 6/2009 | Koeth et al. | 2005/0039279 A1 | 2/2005 | Koeth et al. |
| 7,562,411 B2 | 7/2009 | Gavney, Jr. | 2005/0049155 A1 | 3/2005 | Gavney |
| 7,814,603 B2 | 10/2010 | Gavney | 2005/0060826 A1 | 3/2005 | Gavney |

| Publication No. | Date | Name |
|---|---|---|
| 2005/0066456 A1 | 3/2005 | Gavney |
| 2005/0066462 A1 | 3/2005 | Moskovich et al. |
| 2005/0069372 A1 | 3/2005 | Hohlbein et al. |
| 2005/0071939 A1 | 4/2005 | Wong |
| 2005/0091767 A1 | 5/2005 | Jimenez et al. |
| 2005/0091769 A1 | 5/2005 | Jimenez et al. |
| 2005/0091773 A1 | 5/2005 | Gavney et al. |
| 2005/0097693 A1 | 5/2005 | Bransky et al. |
| 2005/0107017 A1 | 5/2005 | Fioratti |
| 2005/0138743 A1 | 6/2005 | Huber et al. |
| 2005/0138744 A1 | 6/2005 | Hohlbein |
| 2005/0138745 A1 | 6/2005 | Huang |
| 2005/0155172 A1 | 7/2005 | Gavney |
| 2005/0160541 A1 | 7/2005 | Goldfine |
| 2005/0166341 A1 | 8/2005 | Solanki |
| 2005/0166343 A1 | 8/2005 | Gavney, Jr. ............... 15/110 |
| 2005/0188487 A1 | 9/2005 | Moskovich et al. |
| 2005/0188488 A1 | 9/2005 | Moskovich et al. |
| 2005/0188489 A1 | 9/2005 | Hohlbein |
| 2005/0193512 A1 | 9/2005 | Moskovich et al. |
| 2005/0198753 A1 | 9/2005 | Berede et al. |
| 2005/0198757 A1 | 9/2005 | Gavney et al. |
| 2005/0210612 A1 | 9/2005 | Hohlbein et al. |
| 2005/0210613 A1 | 9/2005 | Wagstaff |
| 2005/0235439 A1 | 10/2005 | Braun et al. |
| 2005/0241091 A1 | 11/2005 | Foster et al. |
| 2005/0229339 A1 | 12/2005 | Gavney et al. |
| 2005/0273952 A1 | 12/2005 | Chan et al. |
| 2005/0273954 A1 | 12/2005 | Gavney |
| 2005/0273961 A1 | 12/2005 | Moskovich et al. |
| 2005/0278883 A1 | 12/2005 | Hohlbein |
| 2006/0000036 A1 | 1/2006 | Eliav et al. |
| 2006/0010623 A1 | 1/2006 | Crossman et al. |
| 2006/0010628 A1 | 1/2006 | Moskovich |
| 2006/0010631 A1 | 1/2006 | Geiberger |
| 2006/0021170 A1 | 2/2006 | Gavney |
| 2006/0026784 A1 | 2/2006 | Moskovich et al. |
| 2006/0037160 A1 | 2/2006 | Kayser |
| 2006/0059642 A1 | 2/2006 | Solanki |
| 2006/0064827 A1 | 3/2006 | Chan |
| 2006/0064833 A1 | 3/2006 | Jacobs |
| 2006/0075588 A1 | 4/2006 | Amador |
| 2006/0085932 A1 | 4/2006 | Santos |
| 2006/0107474 A1 | 5/2006 | McDougall |
| 2006/0107478 A1 | 5/2006 | Boucherie ............... 15/167.1 |
| 2006/0117506 A1 | 6/2006 | Gavney et al. |
| 2006/0117508 A1 | 6/2006 | Hohlbein |
| 2006/0230563 A1 | 10/2006 | Gavney |
| 2006/0236477 A1 | 10/2006 | Gavney |
| 2006/0240380 A1 | 10/2006 | Chenvainu et al. ............ 433/80 |
| 2007/0033755 A1 | 2/2007 | Gavney |
| 2007/0074361 A1 | 4/2007 | Gavney |
| 2007/0271717 A1 | 11/2007 | Clos et al. |
| 2008/0201885 A1 | 8/2008 | Moskovich |
| 2009/0282628 A1 | 11/2009 | Braun |

FOREIGN PATENT DOCUMENTS

| | | |
|---|---|---|
| DE | 19717868 | 10/1998 |
| DE | 10122987 A1 | 11/2002 |
| DE | 20111428 | 1/2003 |
| DE | 10164336 | 7/2003 |
| EP | 0 360 766 | 3/1990 |
| EP | 0 968 686 A1 | 1/2000 |
| EP | 1004282 | 5/2000 |
| EP | 1 080 664 | 3/2001 |
| EP | 0918477 | 3/2003 |
| EP | 1584263 | 10/2005 |
| EP | 1 661 487 | 5/2006 |
| EP | 1 700 537 A1 | 9/2006 |
| FR | 936529 | 7/1948 |
| FR | 2 196 782 | 3/1974 |
| FR | 2636818 | 3/1990 |
| GB | 2040161 | 1/1979 |
| GB | 2371217 | 7/2002 |
| JP | 26008198 | 7/1949 |
| JP | 1937018465 | 7/1970 |
| JP | 1971013226 | 5/1971 |
| JP | 5107676 U | 6/1976 |
| JP | 197810671 | 1/1978 |
| JP | 198099210 | 7/1980 |
| JP | 1989500490 | 2/1989 |
| JP | 1-72128 | 3/1989 |
| JP | 1989086822 | 6/1989 |
| JP | 1990089925 | 7/1990 |
| JP | 19979019323 | 1/1997 |
| JP | 1997502118 | 3/1997 |
| JP | 19988262733 | 10/1998 |
| JP | 1997-140456 | 12/1998 |
| JP | 11332651 | 12/1999 |
| JP | 2000-157338 | 6/2000 |
| JP | 2000-300345 | 10/2000 |
| JP | 2000-300347 | 10/2000 |
| JP | 2000300342 | 10/2000 |
| JP | 2000-308524 | 11/2000 |
| JP | 2001070043 | 3/2001 |
| JP | 2001178540 | 7/2001 |
| JP | 2001504024 | 7/2001 |
| JP | 2001275751 | 10/2001 |
| JP | 2001286343 | 10/2001 |
| JP | 2002010832 | 1/2002 |
| JP | 2002500903 | 1/2002 |
| JP | 2002034657 | 5/2002 |
| JP | 2002514946 | 5/2002 |
| JP | 2002199938 | 7/2002 |
| JP | 2003153741 | 5/2003 |
| JP | 2003225122 | 8/2003 |
| JP | 2003523788 | 8/2003 |
| JP | 2005305116 | 11/2004 |
| JP | 2004538029 | 12/2004 |
| RU | 2 161 018 C2 | 12/2000 |
| WO | WO 87/00032 | 1/1987 |
| WO | WO8700032 A2 | 1/1987 |
| WO | 8707500 | 12/1987 |
| WO | WO 94/03125 | 2/1994 |
| WO | 9609781 | 4/1996 |
| WO | 9615696 | 5/1996 |
| WO | WO 96/20654 | 7/1996 |
| WO | WO 96/28994 | 9/1996 |
| WO | 9716995 | 5/1997 |
| WO | WO 98/11843 | 3/1998 |
| WO | WO 98/18364 | 5/1998 |
| WO | 0049911 | 8/2000 |
| WO | 0064307 | 11/2000 |
| WO | 0774522 | 12/2000 |
| WO | WO 01/01817 | 1/2001 |
| WO | WO0121036 A1 | 3/2001 |
| WO | 0126505 | 4/2001 |
| WO | WO 02/11583 A2 | 2/2002 |
| WO | WO2004026077 A1 | 4/2002 |
| WO | WO 02/45617 A1 | 6/2002 |
| WO | WO 03/015575 A1 | 2/2003 |
| WO | WO 03/020076 A1 | 3/2003 |
| WO | WO03030680 A1 | 4/2003 |
| WO | WO03043459 A2 | 5/2003 |
| WO | WO 03/055351 A1 | 7/2003 |
| WO | WO 03/086140 A1 | 10/2003 |
| WO | WO 2004/014181 A1 | 2/2004 |
| WO | WO2004014182 A1 | 2/2004 |
| WO | WO2004014183 A1 | 2/2004 |
| WO | WO2004016188 A2 | 2/2004 |
| WO | WO 2004/028235 A2 | 4/2004 |
| WO | WO 2004/062519 A2 | 7/2004 |
| WO | WO 2004/062573 A2 | 7/2004 |
| WO | WO 2004/071237 A1 | 8/2004 |
| WO | WO2005084486 A1 | 9/2005 |
| WO | WO2006005624 A2 | 1/2006 |
| WO | 2006/012974 | 2/2006 |

OTHER PUBLICATIONS

Office action from the foreign patent office in a counterpart application (European Application No. 04 705 730.2) dated May 2, 2007.
Office Action for U.S. Appl. No. 11/569,789 dated Nov. 24, 2009; P&G Case No. Z-7941Q; Kunath; Filing Date Nov. 29, 2006.

* cited by examiner

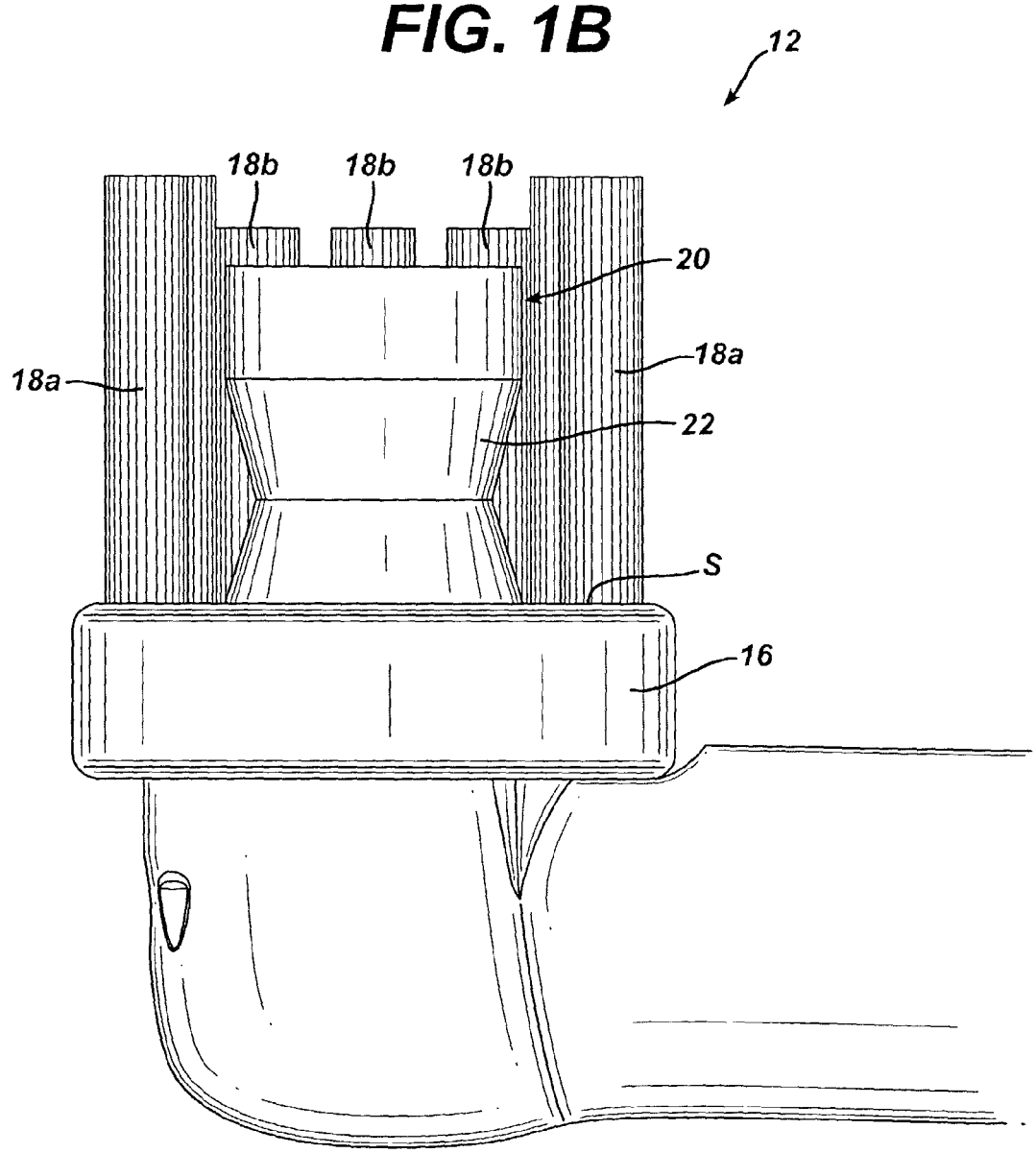

TOOTHBRUSHES

TECHNICAL FIELD

This invention relates to toothbrushes, and more particularly to power toothbrushes.

BACKGROUND

Power toothbrushes are well known and have been on the market for years. In typical power toothbrushes, tufts of bristles on the brush head extend generally perpendicularly from the top surface of the head. The head is oscillated, rotated and/or translated in order to provide enhanced tooth cleaning capability.

SUMMARY

In one aspect, the invention features a toothbrush head that includes a support member, a resilient member extending from the support member, and a plurality of bristles or tufts of bristles extending from the support member and at least partially surrounding the resilient member. By "resilient member" we mean a unitary structure formed of a resilient material such as an elastomer or foam, the resilient member having a perimeter, when the resilient member is viewed from above (e.g., looking down the long axis of the bristles, if the bristles and resilient member are disposed perpendicular to the support member), which circumscribes an area greater than the surface area of the resilient member that will initially contact the teeth of a user of the toothbrush. By "initially contact the teeth," we mean the surface area that will contact the teeth and/or gums prior to any significant deformation of the resilient member resulting from the application of pressure against the teeth, i.e., the area that would contact the teeth if the toothbrush were lightly touched to the teeth with the power turned off. By "unitary structure," we mean that, if the resilient member includes a plurality of elements, such as fins, protrusions or lammelae, the elements are integrally joined to form a single structure that is mounted on the separate support member.

In one aspect, the resilient member may be cup-shaped.

The term "cup-shaped," as used herein, refers to a shape that is generally elliptical, oval, ovoid, or circular in cross-section and that defines a central open area. The walls of the cup-shaped member may be continuous or discontinuous and may define a cylinder, cone, frustroconical shape, or other desired shape. The bottom of the central open area may be flat, concave, or any other desired shape.

In another aspect, the resilient member may be fan-shaped.

The term "fan-shaped," as used herein, refers to a shape that is generally comprised of a central hub region and at least two protrusions, e.g., ribs, fins, or other types of protrusions, that extend substantially radially from the central hub region. The protrusions may form a helix, spiral, screw, or other pattern. The central hub region may be solid, hollow, or cup-shaped, and may be, for example, generally elliptical, oval, ovoid, or circular in cross-section.

In a third aspect, the resilient member is "textured."

The term "textured," as used herein, refers to a structure that has a macroscopic surface texture. For example, the textured member may be composed of a cluster of ribs, fins, columns, or other protrusions, or a combination of ribs, fins, columns, or other protrusions, that together form a unitary structure. As other examples, the texture can be imparted to the member by a manufacturing process such as injection molding, by embedding particles in the surface of the member, or by selecting a material for the member that inherently has a surface texture, e.g., an open cell foam.

Some implementations include one or more of the following features.

The toothbrush head is configured for use on a power toothbrush. The cup-shaped, fan-shaped or textured member comprises a resilient material.

The cup-shaped member defines an open central area having a depth of from about 2 to 5 mm. The cup-shaped member includes a side wall that is substantially continuous. The cup-shaped member includes a plurality of segments that define a discontinuous side wall. The cup-shaped member includes a generally cylindrical, conical or frustroconical side wall.

The toothbrush head further includes a plurality of fin members extending inwardly from an inner surface of the cup-shaped member. The fins have different lengths, heights, and/or thicknesses. At least some of the fin members converge to intersect at a central hub. The central hub has a shape selected from the group consisting of cones, inverted cones, cups and cylinders. The converging fin members increase in height with increasing radial distance from the central hub. The cup-shaped member includes a wavy edge.

The toothbrush head further includes one or more inner cup-shaped members disposed concentrically within an open area defined by the cup-shaped member. The cup-shaped member and inner cup-shaped members are comprised of segments that define discontinuous outer walls of the cup-shaped members.

At least some of the tufts have different heights. The height of the bristle tufts is greater than the height of the cup-shaped member.

The fan-shaped member includes a plurality of protrusions extending radially from a central hub. The central hub is generally cylindrical or conical.

The textured member includes a plurality of lammelae extending from a common base. The textured member includes a molded element having an integrally molded surface texture. The textured member comprises a resilient member formed of a material having a macroscopic surface texture.

The invention also features methods of using and making the toothbrush heads described above.

In some implementations, the toothbrush head provides gum massaging and stimulation in addition to cleaning. The cup-shaped member may help position the toothbrush head on each individual tooth during brushing. This positioning of the head may in turn assist the user in obtaining a proper tooth-to-tooth brushing technique, rather than using a scrubbing motion. This seating action also helps to position the bristles surrounding the cup-shaped member to more effectively access areas between the teeth and along the gumline. In addition, the cup-shaped member may help hold the toothpaste against the teeth during brushing. As a result, toothbrushing may be less messy, and the toothbrush head may be able to hold more toothpaste. Also, toothpaste may tend to be concentrated against the tooth surface, which may in turn result in improved whitening, stain removal, and cleaning. The cup-shaped member may also enhance plaque removal. In some embodiments, the cup-shaped member may be designed to enhance the foaming action of toothpaste.

In other implementations, the toothbrush head may provide enhanced surface cleaning by the motion of the fan-shaped or textured member, both of which provide a wiping action. The increased contact area of the member with the surface of the tooth may also provide enhanced whitening and stain removal.

Other features and advantages of the invention will be apparent from the description and drawings, and from the claims.

DESCRIPTION OF DRAWINGS

FIG. 1B is a side view of FIG. 1A.

DETAILED DESCRIPTION

Figure 1:
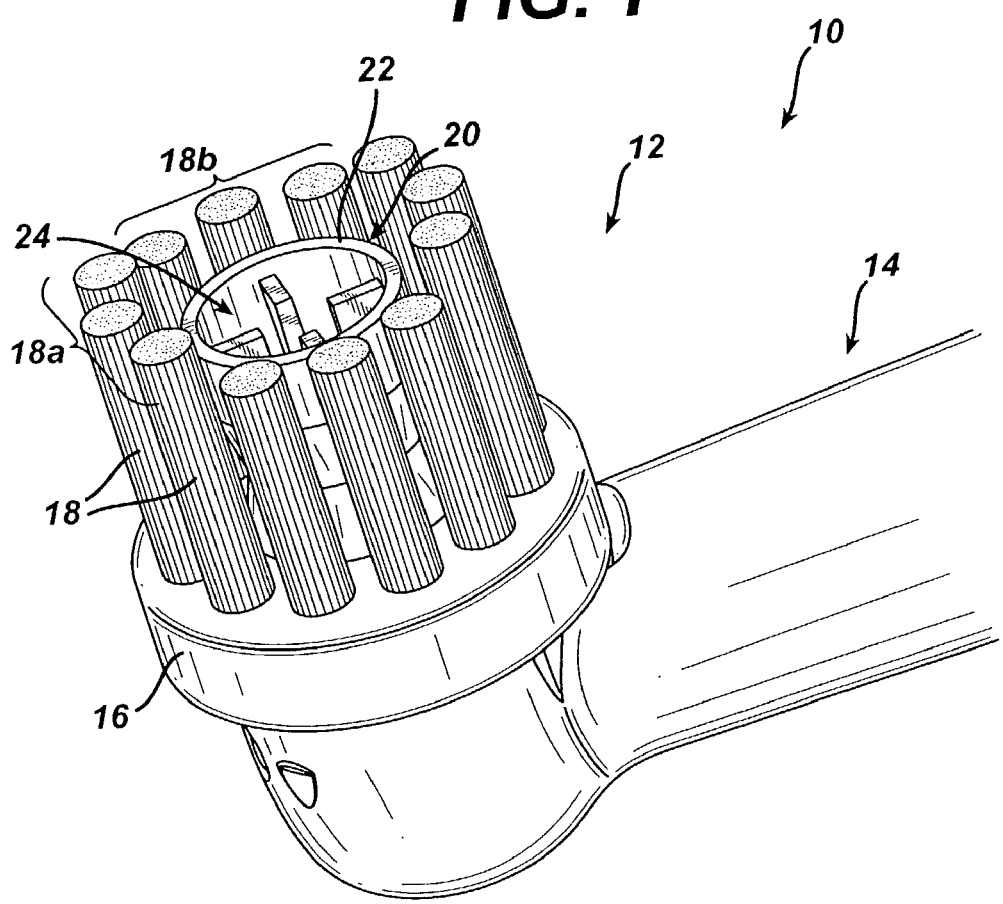
FIG. 1 is a perspective view of a portion of a power toothbrush, according to a first embodiment of the invention.

Referring to FIG. 1, a power toothbrush 10 includes a head 12 and a neck 14. As is well known to those skilled in the art, head 12 is oscillated during brushing. An electric motor (not shown) oscillates the head through gearing, linkages, cranks, and/or other drive mechanisms as is well known. Electrical power may be supplied to the motor by rechargeable or single use (disposable) batteries. Further details as to how the head is oscillated will not be provided, as this aspect of the brush is not the focus of the invention.

Head 12 includes a generally circular support member 16, and, extending from the support member 16, a plurality of bristle tufts 18. Although each tuft is shown as a solid mass in the drawings, the tufts are actually each made up of a great mass of individual plastic bristles. The bristles may be made of any desired polymer, e.g., nylon 6.12 or 6.10, and may have any desired diameter, e.g., 4-8 mil. The tufts are supported at their bases by the support member, and may be held in place by any desired tufting technique as is well known in the art, e.g., hot tufting or a stapling process. The tufts may also be mounted to move on the support member, as is well known in the toothbrush art.

Figure 1A:
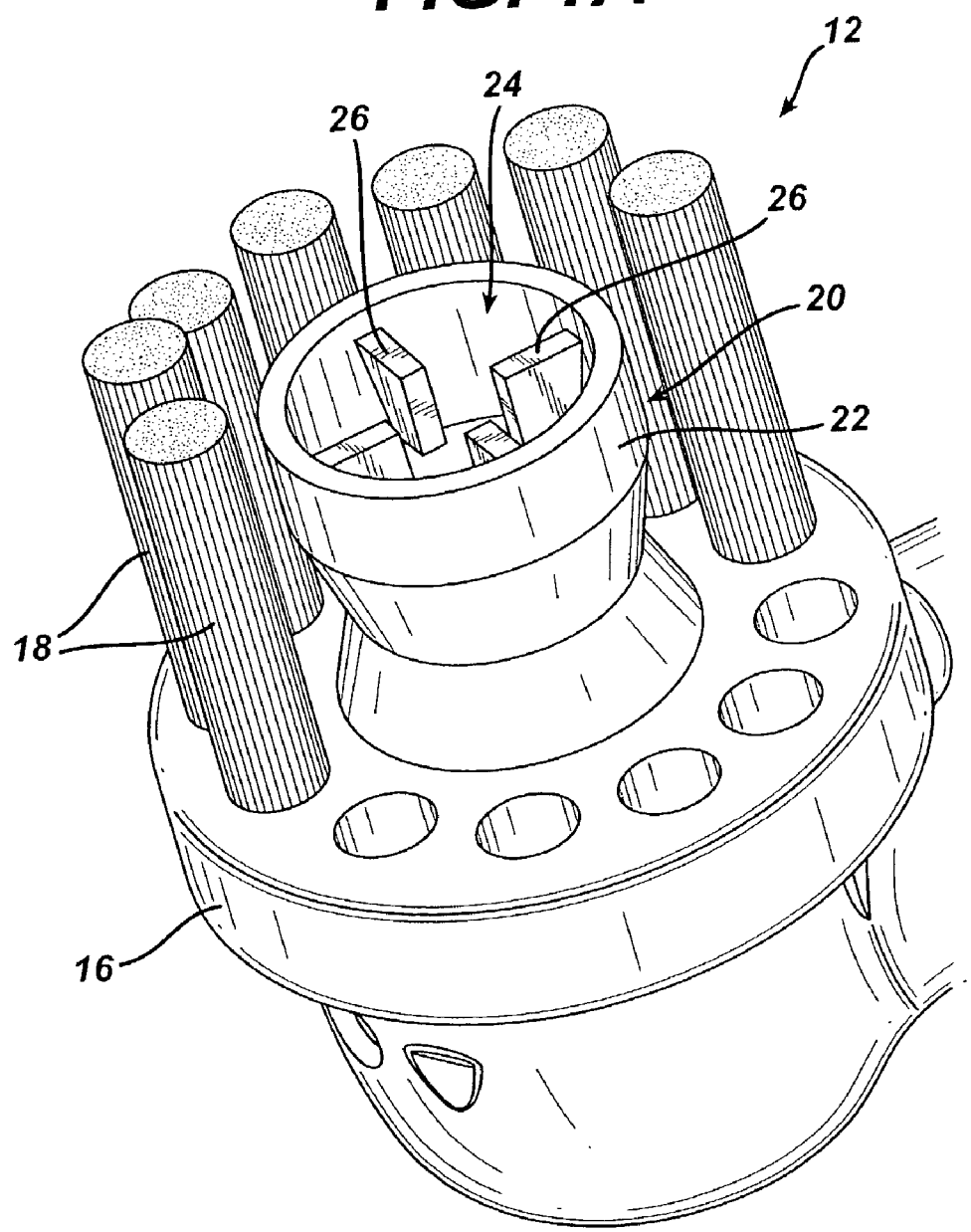
FIG. 1A is similar to FIG. 1, with the front tufts of bristles removed to show the detail of the cup-shaped member.

Head 12 further includes a cup-shaped member 20, which can be seen clearly in FIG. 1A, in which some of the bristle tufts have been omitted. Cup-shaped member 20 includes a side wall 22 that defines a central open area 24. Generally, the central open area 24 has a depth of from about 2 to 5 mm, measured from the highest point of the rim of the cup-shaped member to the lowest point of the central open area. Cup-shaped member 20 also includes a plurality of ribs 26 that extend inwardly into the open area 24. The cup-shaped member 20 is preferably formed of a resilient material such as an elastomer, e.g., a thermoplastic elastomer. The material hardness for such structures may range from 10 to 70 Shore A, with the preferred hardness selection depending on the design and dimensions of the cup-shaped member.

The cup-shaped member 20 may be fixedly mounted on the toothbrush head, or may be rotatably mounted, so that the cup-shaped member 20 can spin about its long axis while the toothbrush head is oscillated. The spinning motion may be driven by the same motor that oscillates the head, as would be understood by those skilled in the art. If the cup-shaped member is fixedly mounted, it may be mounted by any conventional technique, e.g., by screwing it in place or overmolding it onto the support member.

As shown in FIG. 1B, the height of bristle tufts 18 above the top surface S of support member 16 will generally be greater than the height of the cup-shaped member 20 from surface S. This height differential allows the head to contour around each tooth, enhancing the tooth-to-tooth indexing effect mentioned above.

There is also a height differential between the different bristle tufts. The end bristle tufts 18A, i.e., the tufts that are adjacent the long axis of the toothbrush neck 14 when the head 12 is at rest, are taller than the side tufts 18b. For example, the height of the cup-shaped member may be from about 5.5 to 10 mm, with the end tufts 18A being about 20 to 30% taller than the cup-shaped member, e.g., from about 6.6 to 13 mm in height, and the side tufts 18b being about 5 to 15% taller than the cup-shaped member, e.g., about 5.8 to 11.5 mm in height. Making the side tufts shorter than the end tufts allows the longer tufts to reach in between the teeth, while the shorter tufts clean along the gumline.

Toothbrush heads according to other embodiments are shown in FIGS. 2-10. In each of these embodiments, the support members 116 are generally elliptical, rather than circular as shown in FIG. 1. The elliptical shape provides more room for additional bristle tufts, and thus these toothbrush heads further include curved, elongated interdental tufts 28. In these embodiments, the cup-shaped member and bristle tufts are generally shorter than in the embodiment discussed above. In an elliptical head, the reduced height will tend to make the brush more comfortable and less "bulky" feeling in a user's mouth. As in the embodiment discussed above, the bristle tufts are generally taller than the cup-shaped member. As shown in FIG. 2A, the interdental tufts 28 are also taller than the cup-shaped member, e.g., by about 30 to 40%.

Each of the embodiments shown in FIGS. 2-7 includes a different type of cup-shaped member.

Figure 2:
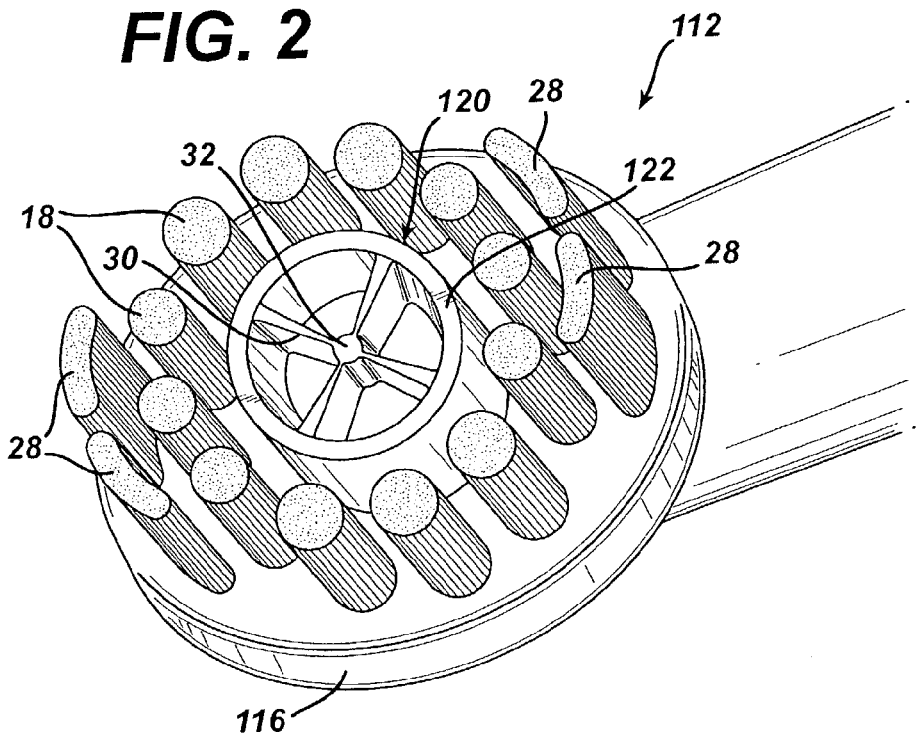
FIG. 2 is a perspective view of a toothbrush head according to an alternative embodiment of the invention.
Figure 3:
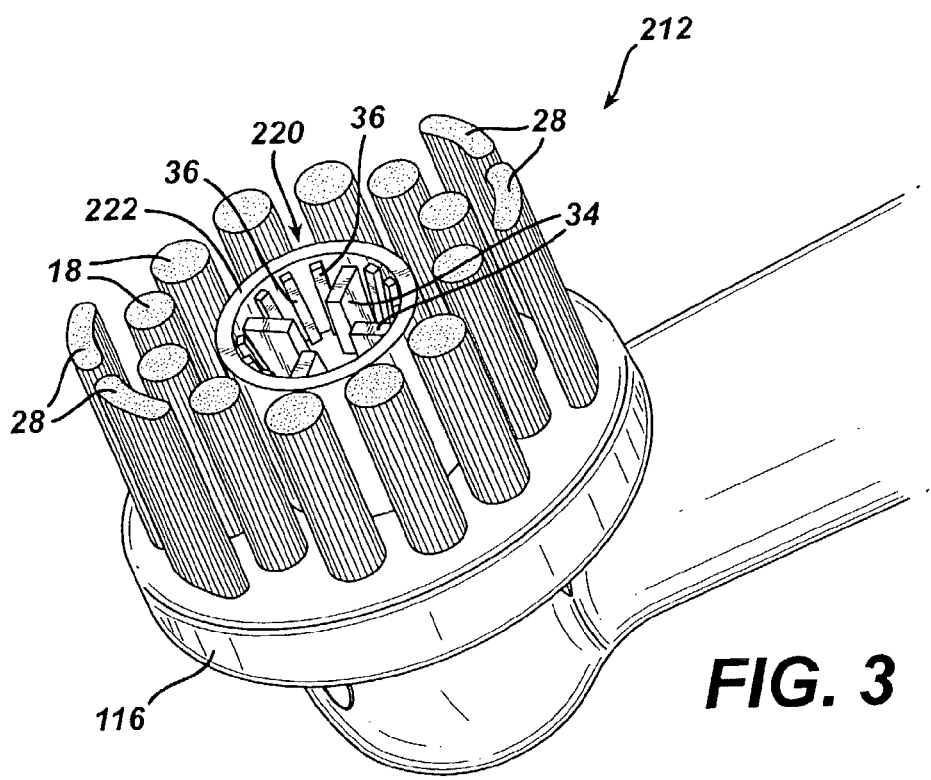
FIGS. 3-10 are perspective views of toothbrush heads according to various alternative embodiments of the invention, with the exception of FIG. 7A, which shows the toothbrush head shown in FIG. 7 with the front tufts of bristles removed to show the detail of the fan-shaped member.
Figure 2A:
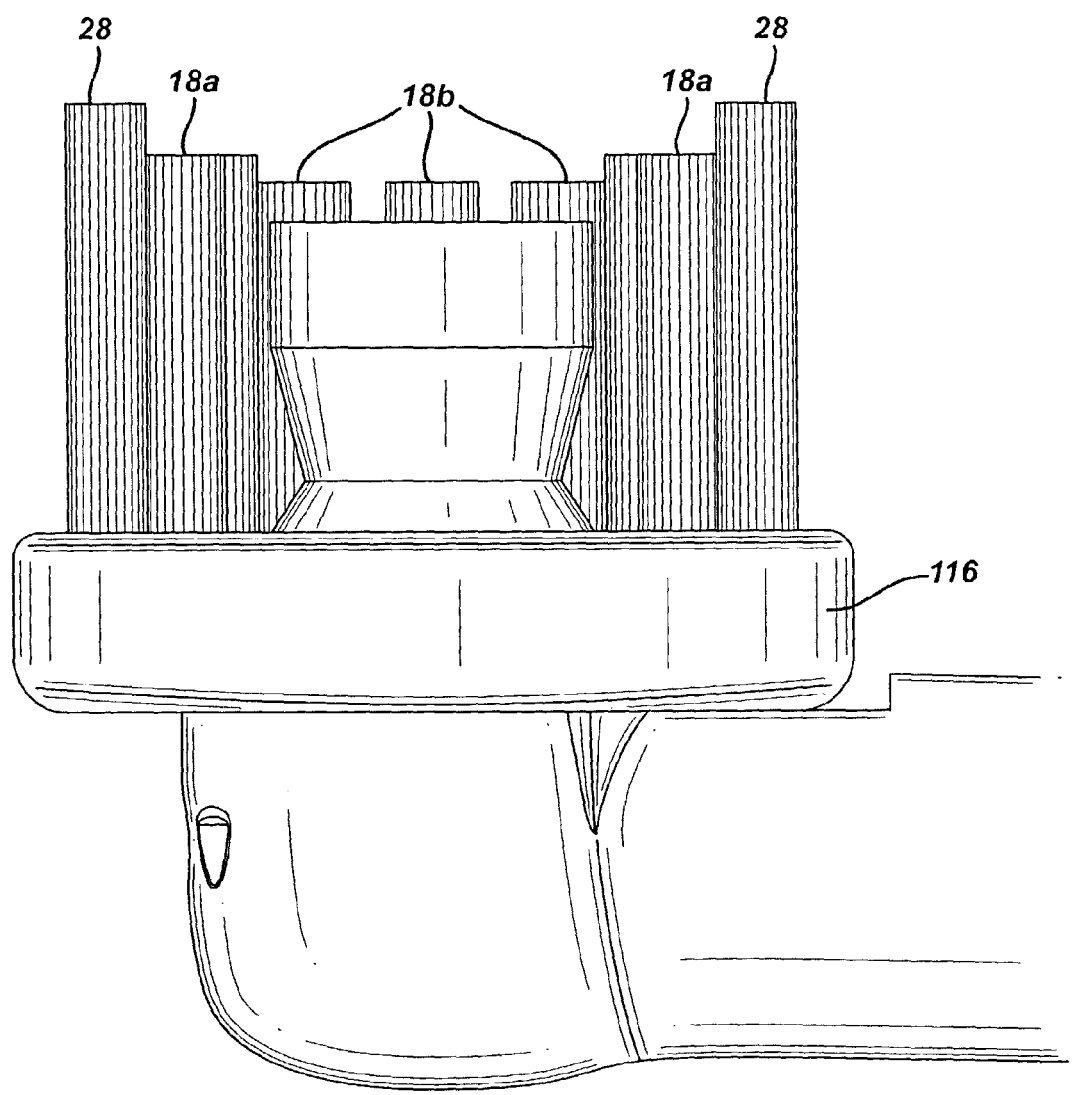
FIG. 2A is a side view of a toothbrush head similar to the one shown in FIG. 2 with the front tufts of bristles removed to show the detail of the cup-shaped member.
Figure 2B:
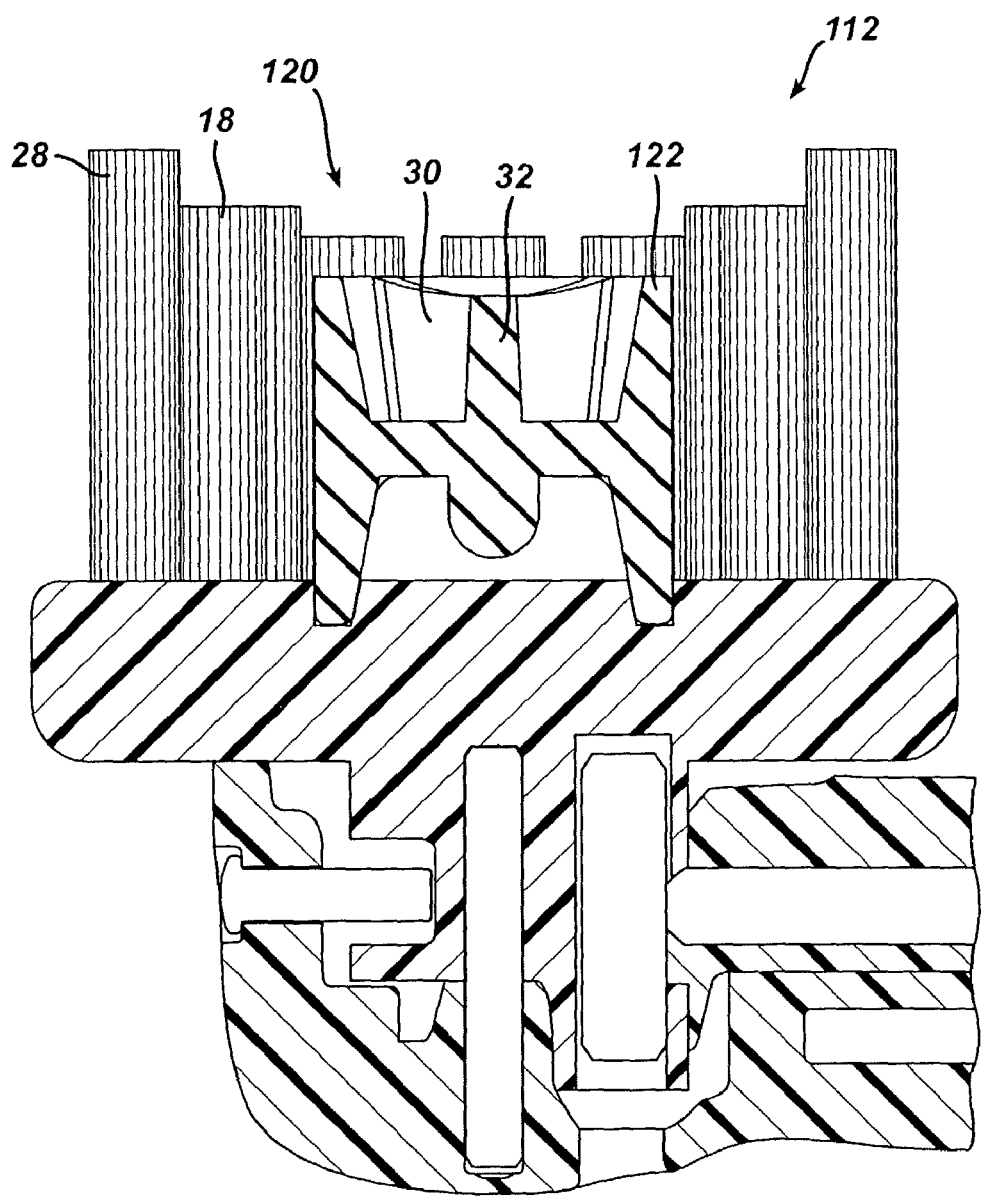
FIG. 2B is a cross-sectional view of the toothbrush head shown in FIG. 2, taken along the long axis of the toothbrush.

In head 112, shown in FIG. 2, cup shaped member 120 includes a side wall 122, and extending inwardly from the side wall, a plurality of ribs 30 that converge at a generally cylindrical central hub 32. In alternate embodiments (not shown) the central hub may be conical or cup-shaped. In this design, as shown in FIG. 2B, the ribs are at the same height as the cup at the outer perimeter, and decrease in height as they approach the center. This arrangement allows the ribs to act as "squeegees" to clean the tooth surface. The addition of the central hub adds strength to the total structure and the ribs. If this additional strength is not required for a particular design, the central hub may be omitted, and the ribs may simply intersect each other, or may stop short of intersecting. In head 212, shown in FIG. 3, cup-shaped member 220 includes a side wall 222 and, extending inwardly from the side wall, a plurality of larger ribs 34 and smaller ribs 36. The larger ribs are longer (i.e., extend further into the center), and may have a different thickness and/or height than the smaller ribs.

Figure 4:
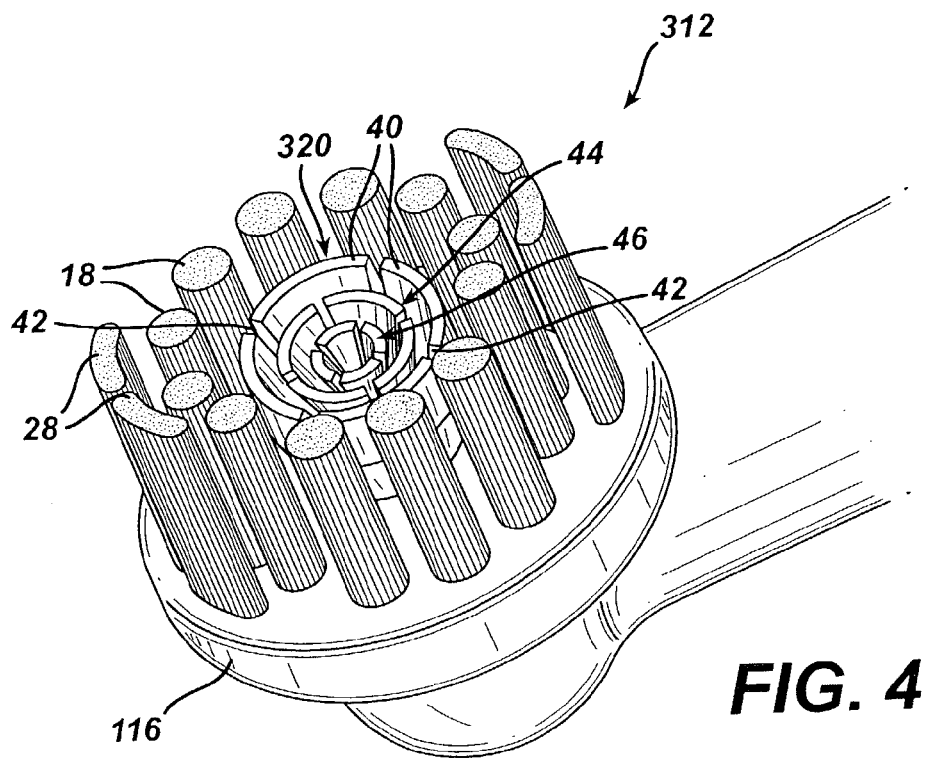
Figure 5:
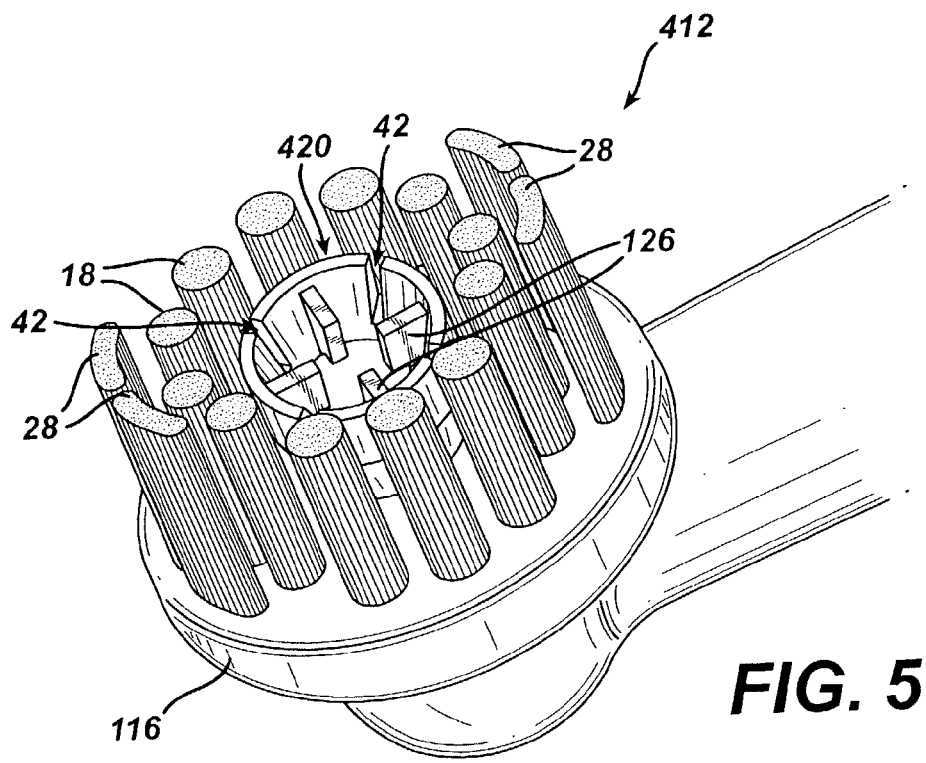

In the embodiments shown in FIGS. 4 and 5, the cup-shaped member is segmented, i.e., it has a discontinuous side wall that includes a plurality of arcuate segments. The segmented structure imparts flexibility to the cup-shaped member, and may allow the cup-shaped member to conform better to the tooth surface. As can be seen in FIG. 5, in these embodiments the segments are defined by grooves 42 that do not extend to the bottom of the cup-shaped member. As a result, the segments are connected to form a unitary structure.

In head 312, shown in FIG. 4, cup-shaped member 320 includes a segmented side wall that includes four arcuate segments 40 having grooves 42 therebetween. Within the open center area defined by the cup-shaped member 320 are disposed two concentrically arranged smaller inner cup-shaped members 44 and 46. These inner cup-shaped members have the same segmented structure as the outer cup-shaped member 320. The concentric members provide a large surface area for contact with the tooth surface, which may provide improved cleaning.

In head 412, shown in FIG. 5, cup-shaped member 420 again includes a segmented side wall comprised of four arcuate segments. In this embodiment, ribs 126 extend inwardly from the side wall, as in the embodiment shown in FIG. 1.

Figure 6:
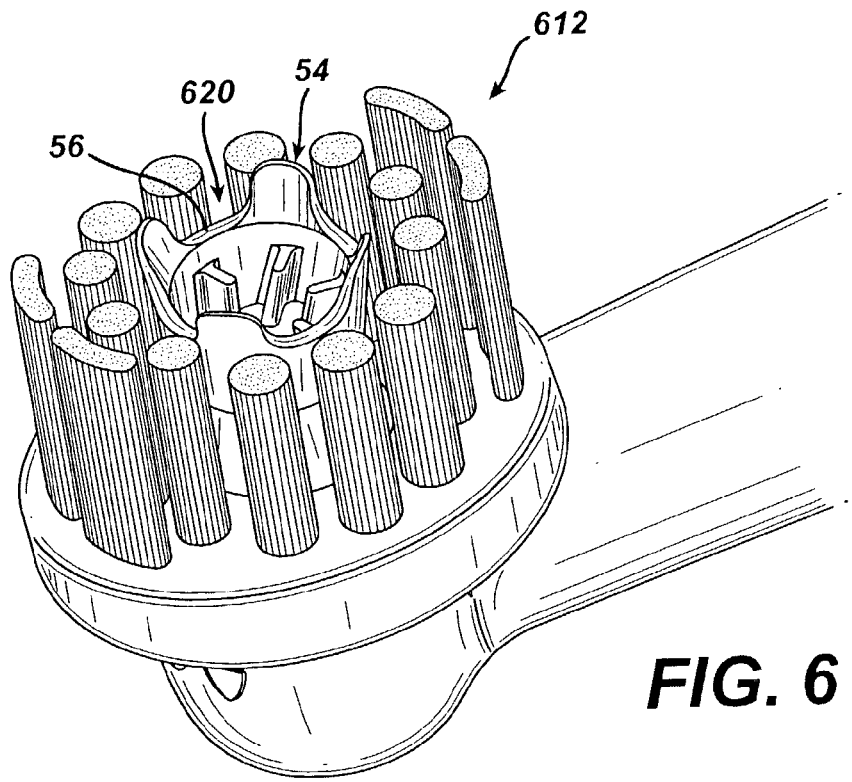

In the embodiment shown in FIG. 6, head 612 includes a cup-shaped member 620 that has a wavy fringe 54 extending above its upper edge 56. The wavy fringe is relatively soft and flexible, so that it will lay flat when pressed against the surface of the teeth. This may allow the fringe to slide under the gums and between the teeth, providing plaque removal and gum stimulation which may reduce gingivitis. Generally, the fringe has a thickness of about 0.15 to 0.25 mm, measured at its top edge, and about 0.4 to 0.8 mm measured at its base (where the fringe joins the rim of the cup-shaped member). While four relatively large waves are shown in FIG. 6, if desired more waves and/or smaller waves may be used. The number and size of the waves are selected to provide desired product attributes.

Head 612 also differs from the designs described above in that the cup-shaped member 620 includes ribs 60 that are inclined with respect to the longitudinal axis of the cup-shaped member.

Figure 7:
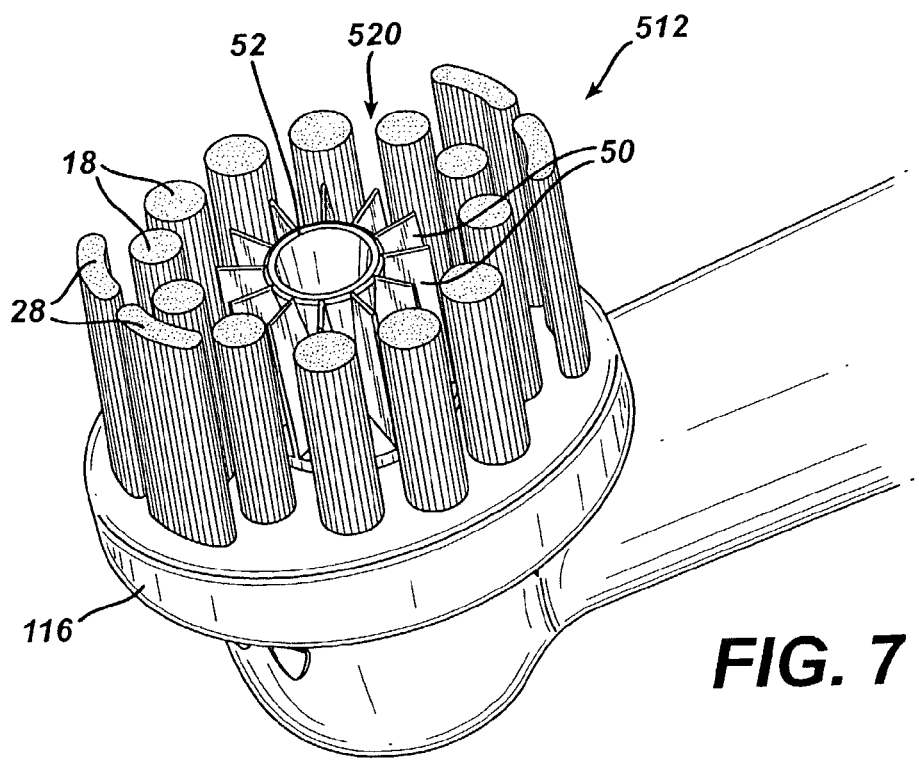
Figure 7A:
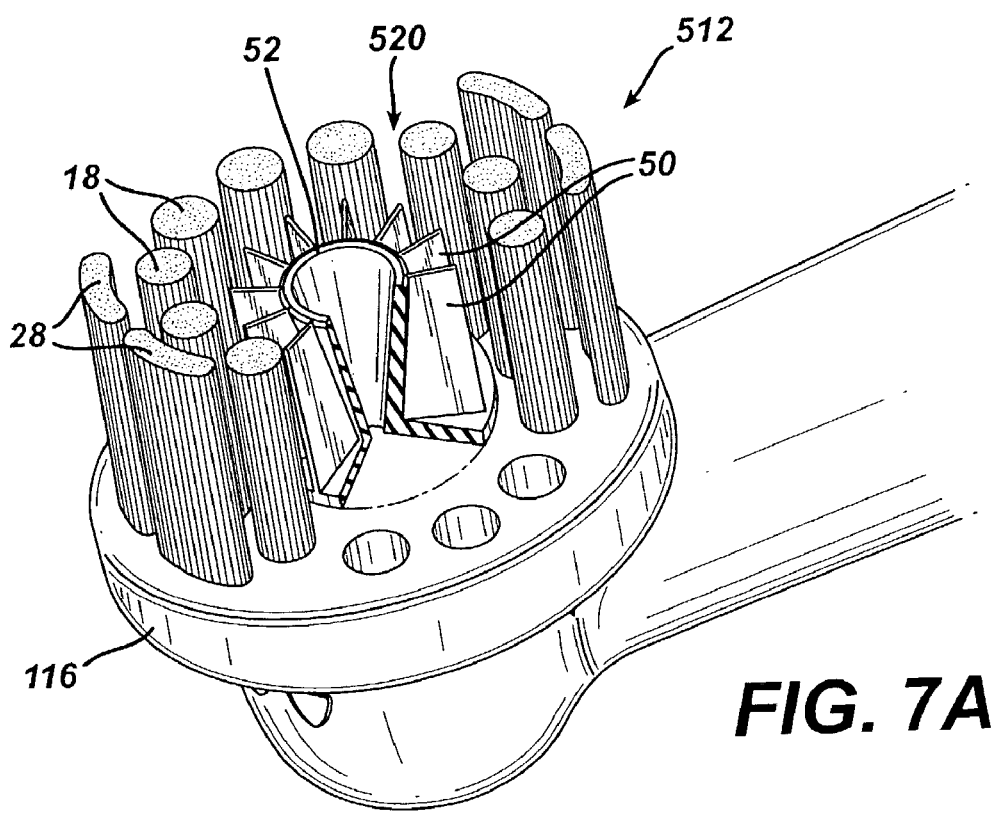

In the embodiment shown in FIG. 7, head 512 includes a fan-shaped member 520 that has a plurality of ribs 50 extending radially from an outer surface of its side wall 52 in a fan-like arrangement. In this embodiment, the side wall 52 is generally conical. Alternatively, if desired, the side wall may be cylindrical (not shown). In this embodiment, the fan-like structure of the cup-shaped member may enhance the foaming action of some toothpastes. The ribs may also act as "squeegees", enhancing tooth-cleaning action.

Figure 8:
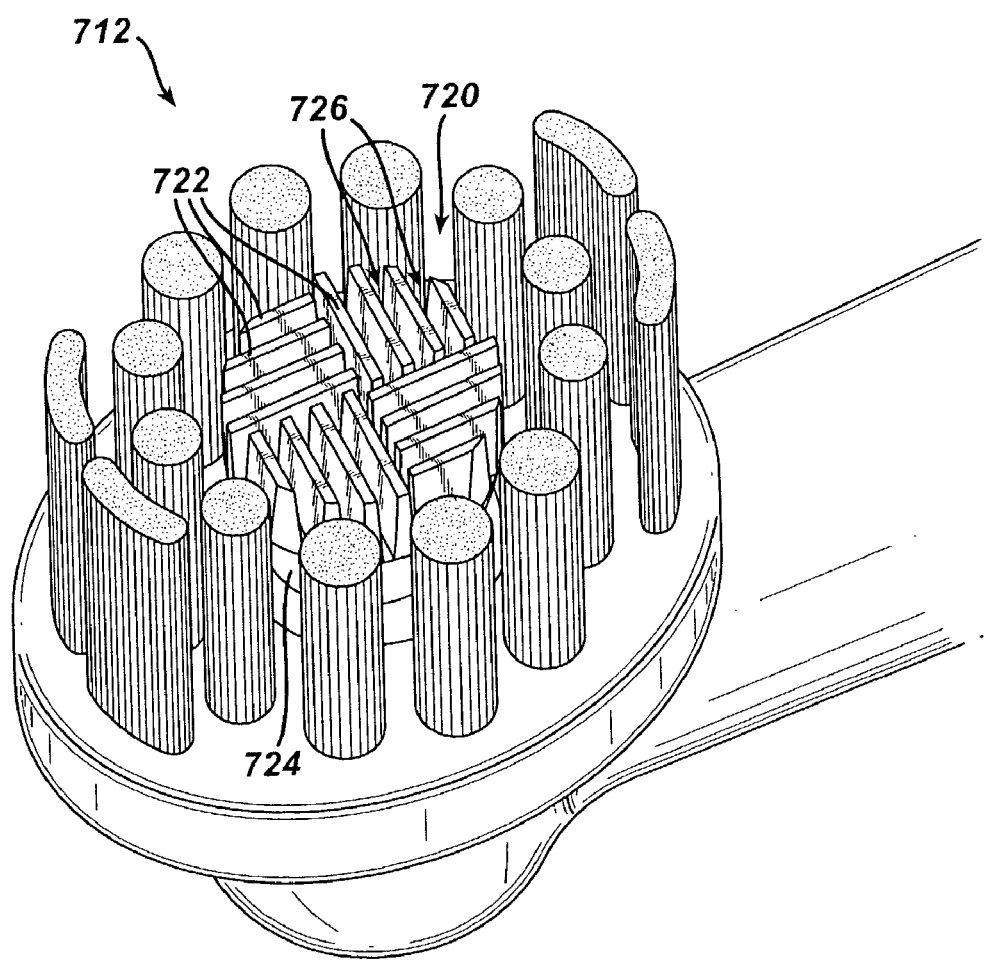

In the embodiment shown in FIG. 8, head 712 includes a textured member 720 that is comprised of a plurality of lammelae 722 that extend from a common base 724 together define a unitary structure. The lammelae 722 are arranged in different directions to give a "textured" feel. In this embodiment, the lammelae define a generally circular member, and are arranged in groups that are at right angles to each other in a "woven" pattern. However, the textured member may have any desired shape and arrangement of lamellae. It is generally preferred that the lammelae be relatively closely spaced, e.g., that spaces 726 be less than about 0.75 mm wide, more preferably about 0.5 mm or less.

Figure 9:
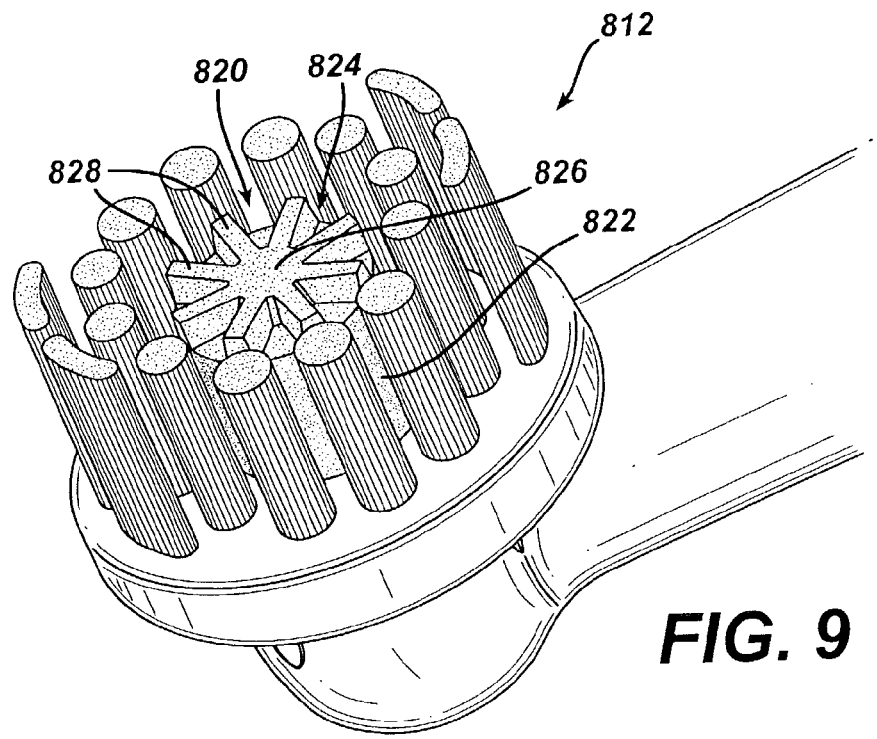

In the embodiment shown in FIG. 9, head 812 includes a textured member 820. Textured member 820 includes a generally cylindrical base 822 and, extending from the base, a contact portion 824 that includes a central hub 826 and a plurality of ribs 828 extending radially from the hub. Textured member 820 may be formed of a foam, as shown, to provide a surface texture.

Figure 10:
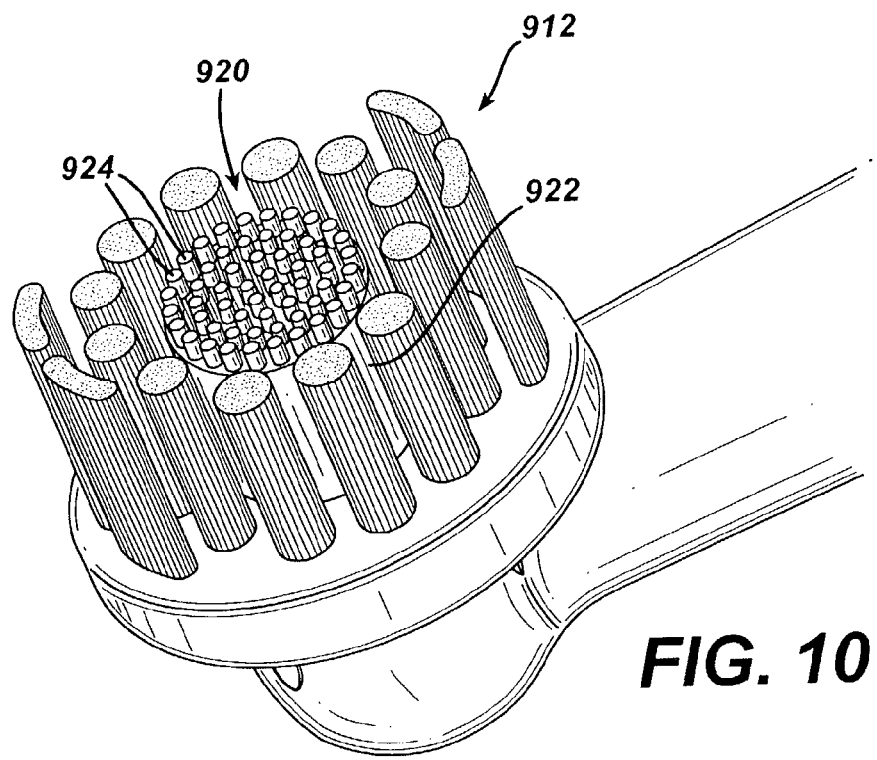

In the embodiment shown in FIG. 10, head 912 includes a textured member 920, including a generally cylindrical base 922 and, extending from the base, a plurality of small nubs 924 that provide the member with a textured feel.

A textured feel may be provided in many ways, for example by forming a resilient member of any desired shape of a material having a macroscopic surface texture, e.g., an open celled foam, or a material having texture-imparting particles embedded in its surface.

Other embodiments are within the scope of the following claims.

For example, while the cup-shaped member is shown in the drawings as centrally-located on the toothbrush head, if desired it may be positioned off-center.

Moreover, while various embodiments are shown in the drawings and described above, many other types of cup-shaped members may be used, as will be well understood by those skilled in the art. For example, the side wall of the cup-shaped member may have a tapered outer surface, or may be straight sided or have any other desired design.

Additionally, which the cup-shaped member is described above as being surrounded on all sides by bristle tufts, if desired the cup-shaped member may be only partially surrounded by bristle tufts. For example, if desired the side tufts 18B in FIG. 1 could be omitted.

Moreover, while heads for power toothbrushes have been described above, resilient members having the features described above may be used on manual toothbrushes, if desired.

What is claimed is:

1. A head for a toothbrush comprising:
a support member configured for releasable attachment to a power toothbrush,
a cup-shaped member extending from the support member, the cup-shaped member including a plurality of fin members extending inwardly from an inner surface of the cup-shaped member, and
a plurality of tufts of bristles extending from the support member and at least partially surrounding the cup-shaped member, wherein at least some of the tufts of bristles are about 20 to 30 percent taller than the cup-shaped member.

2. The toothbrush head of claim 1 wherein the cup-shaped member includes a side wall that is substantially continuous.

3. The toothbrush head of claim 1 wherein the cup-shaped member includes a plurality of segments that define a discontinuous side wall.

4. The toothbrush head of claim 1 wherein the cup-shaped member includes a cylindrical side wall.

5. The toothbrush head of claim 1 wherein the cup-shaped member includes a conical or frustroconical side wall.

6. The toothbrush head of claim 1 wherein the cup-shaped member includes a wavy edge.

7. The toothbrush head of claim 1 wherein at least some of the fin members converge to intersect at a central hub.

8. The toothbrush head of claim 7 wherein the central hub has a shape selected from the group consisting of cones, inverted cones, cups and cylinders.

9. The toothbrush head of claim 7 wherein the converging fin members increase in height with increasing radial distance from the central hub.

10. The toothbrush head of claim 1 wherein the fins have different lengths.

11. The toothbrush head of claim 1 wherein the fins have different thicknesses.

12. The toothbrush head of claim 1 wherein the fins have different heights.

13. The toothbrush head of claim 1 wherein the cup-shaped member defines an open central area having a depth of from about 2 to 5 mm.

14. The toothbrush head of claim 1 wherein the cup-shaped member comprises a material having texture-imparting particles embedded in its surface.

15. The toothbrush head of claim 1, wherein there is a height differential between at least some of the bristle tufts.

16. A power toothbrush comprising:
(a) a handle;
(b) a head configured for releasable attachment to the handle, the head including:
  (i) a support member,
  (ii) a cup-shaped member extending from the support member, the cup-shaped member including a plurality of fin members extending inwardly from an inner surface of the cup-shaped member, and
  (iii) a plurality of tufts of bristles extending from the support member and at least partially surrounding the cup-shaped member, wherein at least some of the tufts of bristles are about 20 to 30 percent taller than the cup-shaped member; and
(c) a drive mechanism, disposed within the handle, configured to drive the head.

* * * * *